US012714736B2

(12) United States Patent
Kohn et al.

(10) Patent No.: US 12,714,736 B2
(45) Date of Patent: Aug. 25, 2026

(54) METHODS FOR PREVENTING AN IMMUNOGLOBULIN E-RELATED DISEASE

(71) Applicant: MY-OR DIAGNOSTICS LTD., Zikhron Yaakov (IL)

(72) Inventors: Ron Kohn, Kefar Uriya (IL); Michael Brandwein, Elazar (IL); Ariel Katz, Zikhron Yaakov (IL)

(73) Assignee: MY-OR DIAGNOSTICS LTD., Zikhron Yaakov (IL)

( * ) Notice: Subject to any disclaimer, the term of this patent is extended or adjusted under 35 U.S.C. 154(b) by 967 days.

(21) Appl. No.: 17/633,684

(22) PCT Filed: Aug. 11, 2020

(86) PCT No.: PCT/IL2020/050875

§ 371 (c)(1),
(2) Date: Feb. 8, 2022

(87) PCT Pub. No.: WO2021/028908

PCT Pub. Date: Feb. 18, 2021

(65) Prior Publication Data

US 2022/0313768 A1 Oct. 6, 2022

Related U.S. Application Data

(60) Provisional application No. 62/989,754, filed on Mar. 15, 2020, provisional application No. 62/885,263, filed on Aug. 11, 2019.

(51) Int. Cl.

| | |
|---|---|
| ***A61K 36/886*** | (2006.01) |
| ***A61P 11/06*** | (2006.01) |
| ***A61P 37/02*** | (2006.01) |
| ***A61P 37/08*** | (2006.01) |

(52) U.S. Cl.

CPC ............ *A61K 36/886* (2013.01); *A61P 11/06* (2018.01); *A61P 37/02* (2018.01); *A61P 37/08* (2018.01)

(58) Field of Classification Search

None

See application file for complete search history.

(56) References Cited

U.S. PATENT DOCUMENTS

| | | | | |
|---|---|---|---|---|
| 2010/0285110 | A1 | 11/2010 | Cid Vivanco et al. | |
| 2016/0243164 | A1* | 8/2016 | Yates .................... | A61K 33/38 |

OTHER PUBLICATIONS

Lakeridge Health “Asthma Attack Prevention” Jul. 2016, https://www.lakeridgehealth.on.ca/en/ourservices/resources/ED-Discharge-instructions/Asthma-Attack-Prevention-revised.pdf (accessed Mar. 7, 2025) (Year: 2016).*

Cleveland Clinic “Asthma” 2025, https://www.mayoclinic.org/diseases-conditions/asthma/symptoms-causes/syc-20369653#:~:text=While%20there%27s%20no%20way%20to,and%20managing%20an%20asthma%20attack (accessed Mar. 7, 2025) (Year: 2025).*

Cleveland Clinic “Food Allergies” 2025, https://my.clevelandclinic.org/health/diseases/9196-food-allergies (accessed Mar. 8, 2025) (Year: 2025).*

Lowe et al. “The skin as a target for prevention of the atopic march” Ann. Allergy Asthma Immunol. 2018, 120, 145-151 (Year: 2018).*

Benton et al. “Environmental Factors Contribute to the Onset of Food Allergies” J. Environ. Sci. Public Health 2017, 1(1), 27-43 (Year: 2017).*

Kelleher et al. “Skin barrier impairment at birth predicts food allergy at 2 years of age” J. Allergy Clin. Immunol. 2016, 137(4), 1111-1116 (Year: 2016).*

O’Donovan et al. “Cohort profile: The Cork Baseline Birth Cohort Study: Babies after Scope: Evaluating the Longitudinal Impact on Neurological and Nutritional Endpoints”, International Journal of Epidemiology 2015, 44(3), 764-775 (Year: 2015).*

Dawid-Pać “Medicinal plants used in treatment of inflammatory skin disease” Postep. Derm. Alergol. 2013, 3, 170-177 (Year: 2013).*

Ahn K. The role of air pollutants in atopic dermatitis. J Allergy Clin Immunol. Nov. 2014; 134(5):993-9; discussion 1000. doi: 10.1016/j.jaci.2014.09.023. Epub Nov. 5, 2014. PMID: 25439225.

PM Elias, R Sun, AR Eder, JS Wakefield & M-Q Man (2013) Treating atopic dermatitis at the source: corrective barrier repair therapy based upon new pathogenic insights, Expert Review of Dermatology, 8:1, 27-36, DOI: 10.1586/edm.12.73.

Janeway CA Jr, Travers P, Walport M, et al. Immunobiology: The Immune System in Health and Disease. Chapter 12. 5th edition. New York: Garland Science; 2001.

Kelleher MM, Dunn-Galvin A, Gray C, Murray DM, Kiely M, Kenny L, McLean WHI, Irvine AD, Hourihane JO. Skin barrier impairment at birth predicts food allergy at 2 years of age. J Allergy Clin Immunol. Apr. 2016; 137(4):1111-1116.e8. doi: 10.1016/j.jaci.2015.12.1312. Retraction in: J Allergy Clin Immunol. Apr. 2021;147(4):1527. PMID: 26924469.

Lowe AJ, Leung DYM, Tang MLK, Su JC, Allen KJ. The skin as a target for prevention of the atopic march. Ann Allergy Asthma Immunol. Feb. 2018;120(2):145-151. doi: 10.1016/j.anai.2017.11.023. PMID: 29413338.

Nopper AJ, Horii KA, Sookdeo-Drost S, Wang TH, Mancini AJ, Lane AT. Topical ointment therapy benefits premature Infants. J Pediatr. May 1996;128(5 Pt 1):660-9. doi: 10.1016/s0022-3476(96)80132-6. PMID: 8627439.

Sierra-Garcia GD, Castro-Rios R, González-Horta A, Lara-Arias J, Chavez-Montes A. Acemannan, an extracted polysaccharide from Aloe vera: A literature review. Nat Prod Commun. Aug. 2014;9(8):1217-21. PMID: 25233608.

McGirt LY, Beck LA. Innate immune defects in atopic dermatitis. J Allergy Clin Immunol. Jul. 2006;118(1):202-8. doi: 10.1016/j.jaci.2006.04.033. Epub Jun. 6, 2006. PMID: 16815156.

(Continued)

*Primary Examiner* — Bethany P Barham
*Assistant Examiner* — Judith Marie Kamm
(74) *Attorney, Agent, or Firm* — The Roy Gross Law Firm, LLC; Roy D. Gross

(57) ABSTRACT

The present invention provides a method of selecting and preventing an IgE-related disease in a subject in need thereof, the method including: (a) selecting a subject at risk of developing an IgE-related disease; and (b) topically administering to the subject a therapeutically effective amount of a composition capable of restoring skin barrier and orally administering to the subject a therapeutically effective amount of a composition including an allergen.

7 Claims, 3 Drawing Sheets

(56) References Cited

OTHER PUBLICATIONS

Bieber T. Atopic dermatitis. N Engl J Med. Apr. 3, 2008;358(14):1483-94. doi: 10.1056/NEJMra074081. PMID: 18385500.

Tauber M, Balica S, Hsu CY, Jean-Decoster C, Lauze C, Redoules D, Viodé C, Schmitt AM, Serre G, Simon M, Paul CF. *Staphylococcus aureus* density on lesional and nonlesional skin is strongly associated with disease severity in atopic dermatitis. J Allergy Clin Immunol. Apr. 2016;137(4):1272-1274.e3. doi: 10.1016/j.jaci.2015.07.052. Epub Nov. 11, 2015. PMID: 26559326.

Clausen ML, Agner T, Lilje B, Edslev SM, Johannesen TB, Andersen PS. Association of Disease Severity With Skin Microbiome and Filaggrin Gene Mutations in Adult Atopic Dermatitis. JAMA Dermatol. Mar. 1, 2018;154(3):293-300. doi: 10.1001/jamadermatol.2017.5440. PMID: 29344612; PMCID: PMC5885821.

Kong HH, Oh J, Deming C, Conlan S, Grice EA, Beatson MA, Nomicos E, Polley EC, Komarow HD; Nisc Comparative Sequence Program, Murray PR, Turner ML, Segre JA. Temporal shifts in the skin microbiome associated with disease flares and treatment in children with atopic dermatitis. Genome Res. May 2012;22(5):850-9. doi: 10.1101/gr.131029.111. Epub Feb. 6, 2012. PMID: 22310478; PMCID: PMC3337431.

Pinart M, et al. Comorbidity of eczema, rhinitis, and asthma in IgE-sensitised and non-IgE-sensitised children in MeDALL: a population-based cohort study. Lancet Respir Med. Feb. 2014;2(2):131-40. doi: 10.1016/S2213-2600(13)70277-7. Epub Jan. 14, 2014. PMID: 24503268.

Du Toit G, Roberts G, Sayre PH, Bahnson HT, Radulovic S, Santos AF, Brough HA, Phippard D, Basting M, Feeney M, Turcanu V, Sever ML, Gomez Lorenzo M, Plaut M, Lack G; Leap Study Team. Randomized trial of peanut consumption in infants at risk for peanut allergy. N Engl J Med. Feb. 26, 2015;372(9):803-13. doi: 10.1056/NEJMoa1414850. Epub Feb. 23, 2015. Erratum in: N Engl J Med. Jul. 28, 2016;375(4):398. PMID: 25705822; PMCID: PMC4416404.

Rodriguez E, Baurecht H, Herberich E, Wagenpfeil S, Brown SJ, Cordell HJ, Irvine AD, Weidinger S. Meta-analysis of filaggrin polymorphisms in eczema and asthma: robust risk factors in atopic disease. J Allergy Clin Immunol. Jun. 2009;123(6):1361-70.e7. doi: 10.1016/j.jaci.2009.03.036. PMID: 19501237.

Jinnestål CL, Belfrage E, Bäck O, Schmidtchen A, Sonesson A. Skin barrier impairment correlates with cutaneous *Staphylococcus aureus* colonization and sensitization to skin-associated microbial antigens in adult patients with atopic dermatitis. Int J Dermatol. Jan. 2014;53(1):27-33. doi: 10.1111/ijd.12198. Epub Jul. 24, 2013. PMID: 23879225.

Kelleher M, Dunn-Galvin A, Hourihane JO, Murray D, Campbell LE, McLean WHI, Irvine AD. Skin barrier dysfunction measured by transepidermal water loss at 2 days and 2 months predates and predicts atopic dermatitis at 1 year. J Allergy Clin Immunol. Apr. 2015;135(4):930-935.e1. doi: 10.1016/j.jaci.2014.12.013. Epub Jan. 22, 2015. Retraction in: J Allergy Clin Immunol. Apr. 2021;147(4):1526. PMID: 25618747; PMCID: PMC4382348.

Horimukai K, Morita K, Narita M, Kondo M, Kabashima S, Inoue E, Sasaki T, Niizeki H, Saito H, Matsumoto K, Ohya Y. Transepidermal water loss measurement during infancy can predict the subsequent development of atopic dermatitis regardless of filaggrin mutations. Allergol Int. Jan. 2016;65(1):103-8. doi: 10.1016/j.alit.2015.09.004. Epub Oct. 29, 2015. PMID: 26666481.

Simpson EL, Chalmers JR, Hanifin JM, Thomas KS, Cork MJ, McLean WH, Brown SJ, Chen Z, Chen Y, Williams HC. Emollient enhancement of the skin barrier from birth offers effective atopic dermatitis prevention. J Allergy Clin Immunol. Oct. 2014;134(4):818-23. doi: 10.1016/j.jaci.2014.08.005. PMID: 25282563; PMCID: PMC4180007.

Horimukai K, Morita K, Narita M, Kondo M, Kitazawa H, Nozaki M, Shigematsu Y, Yoshida K, Niizeki H, Motomura K, Sago H, Takimoto T, Inoue E, Kamemura N, Kido H, Hisatsune J, Sugai M, Murota H, Katayama I, Sasaki T, Amagai M, Morita H, Matsuda A, Matsumoto K, Saito H, Ohya Y. Application of moisturizer to neonates prevents development of atopic dermatitis. J Allergy Clin Immunol. Oct. 2014;134(4):824-830.e6. doi: 10.1016/j.jaci.2014.07.060. PMID: 25282564.

Strid J, Thomson M, Hourihane J, Kimber I, Strobel S. A novel model of sensitization and oral tolerance to peanut protein. Immunology. Nov. 2004;113(3):293-303. doi: 10.1111/j.1365-2567.2004.01989.x. PMID: 15500615; PMCID: PMC1782583.

Strid J, Hourihane J, Kimber I, Callard R, Strobel S. Disruption of the stratum corneum allows potent epicutaneous Immunization with protein antigens resulting in a dominant systemic Th2 response. Eur J Immunol. Aug. 2004;34(8):2100-9. doi: 10.1002/eji.200425196. PMID: 15259007.

Strid J, Hourihane J, Kimber I, Callard R, Strobel S. Epicutaneous exposure to peanut protein prevents oral tolerance and enhances allergic sensitization. Clin Exp Allergy. Jun. 2005;35(6):757-66. doi: 10.1111/j.1365-2222.2005.02260.x. PMID: 15969667.

International search report for PCT/IL2020/050875 dated Dec. 7, 2020.

Written opinion for PCT/IL2020/050875 dated Dec. 7, 2020.

* cited by examiner

METHODS FOR PREVENTING AN IMMUNOGLOBULIN E-RELATED DISEASE

CROSS-REFERENCE TO RELATED APPLICATIONS

This application is a National Phase of PCT Patent Application No. PCT/IL2020/050875 having International filing date of Aug. 11, 2020 which claims the benefit of priority of U.S. Provisional Application No. 62/885,263 titled "METHODS FOR TREATING AN IMMUNOGLOBULIN E-RELATED DISEASE", filed Aug. 11, 2019, and of U.S. Provisional Application No. 62/989,754 titled "METHODS FOR TREATING AN IMMUNOGLOBULIN E-RELATED DISEASE", filed Mar. 15, 2020, the contents of which are all incorporated herein by reference in their entirety.

FIELD OF INVENTION

The present invention, in some embodiments thereof, is in the field of immunoglobulin E (IgE)-related disease diagnosis and therapy.

BACKGROUND

Immunoglobulin E (IgE) is unique amongst immunoglobulins in the sense that it is pivotal in pathophysiology of allergies including chronic inflammatory allergic diseases. Genetic predisposition is characterized by the fact that exposure to particular irritants or allergens induces activity of the IgE (e.g., increased expression, secretion, etc.), which in turn binds to a specific receptor on an immune cell, for example, a mast cell or a basophil.

IgE-related diseases have traditionally been treated with antihistamines, steroids (e.g., corticosteroids), or other anti-inflammatory drugs. Nonetheless, this treatment has not been found to be effective in all patients. The latter may stem from the fact that the therapeutic drug to be administered has to be "tailored" to the specific type of patient (e.g., personalized medicine) or that the disease was lately diagnosed with respect to the "therapeutic window" (i.e., an early diagnosis is crucial for treatment success)

There remains a need for methods of predicting, inhibiting, and preventing the onset of IgE-related diseases.

SUMMARY

According to a first aspect there is provided a method for selecting and preventing an IgE-related disease in a subject, the method comprising: (a) selecting a subject at a risk of developing an IgE-related disease; and (b) topically administering to the subject a therapeutically effective amount of a composition capable of restoring skin barrier and orally administering to the subject a therapeutically effective amount of a composition comprising an allergen, thereby selecting and preventing an IgE-related disease in a subject.

According to another aspect, there is provided a method for determining the suitability of a subject for skin barrier restoration therapy, the method comprising: determining (i) trans epidermal water loss (TEWL) of a forearm of the subject; and (ii) familial history of atopy, food allergy, or both, of the subject, wherein: (i) a TEWL forearm and/or forehead value greater than 7; and (ii) familial history of atopy, food allergy, or both, is indicative of suitability of the subject to skin barrier restoration therapy, thereby determining the suitability of a subject for skin barrier restoration therapy.

In some embodiments, the subject being at a risk of developing an IgE-related disease is characterized by: (i) having a TEWL forearm and/or forehead value greater than 7; and (ii) having familial history of atopy, food allergy, or both.

In some embodiments, the subject being at a risk of developing an IgE-related disease is further characterized by: (iii) being exposed to pollution.

In some embodiments, selecting comprises a step of determining: (a) trans epidermal water loss (TEWL) of a forearm and/or forehead of the subject; and (b) familial history of atopy, food allergy, or both, of the subject.

In some embodiments, selecting comprises a step of determining: (c) whether the subject is or was exposed to pollution.

In some embodiments, the IgE-related disease is selected from the group consisting of: atopic dermatitis, allergic asthma, allergic rhinitis, food allergy, eczema, lupus, rheumatoid arthritis, psoriasis, psoriasis vulgaris, acne, acne vulgaris, rosacea, skin and soft tissue infections, dandruff, blepharitis, tinea versicolor, and any combination thereof.

In some embodiments, the IgE-related disease is atopic dermatitis.

In some embodiments, the IgE-related disease comprises increased amounts of primed basophils, mast cells, or both.

In some embodiments, the composition capable of restoring skin barrier is a cream.

In some embodiments, the composition capable of restoring skin barrier comprises an immuno-stimulator.

In some embodiments, the composition capable of restoring skin barrier comprises a therapeutically effective amount of acemannan.

In some embodiments, acemannan is present in the composition capable of restoring skin barrier in an amount ranging from 0.1 to 1.0% (w/w).

In some embodiments, the composition capable of restoring skin barrier reduces TEWL by at least 20%.

In some embodiments, the composition comprising an allergen is an edible composition.

In some embodiments, the composition comprising an allergen comprises an allergen.

In some embodiments, the composition comprising an allergen comprises a legume, a nut, or a compound derived therefrom.

In some embodiments, administering is daily administering.

In some embodiments, administering is for a period of 2 weeks to 72 months.

In some embodiments, administering starts when the subject is one year old, at most.

In some embodiments, one year old at most, is one month old at most.

In some embodiments, the method further comprises determining (iii) whether the subject is or was exposed to pollution, wherein exposure of the subject to pollution is indicative of suitability of the subject to skin barrier restoration therapy.

In some embodiments, the subject is characterized by having increased amounts of primed basophils, mast cells, or both.

In some embodiments, the subject is at a moderate risk to a very high risk of developing an IgE-related disease.

In some embodiments, the subject is 4 months old at most.

In some embodiments, the skin barrier restoration therapy comprises administration of a pharmaceutical composition, a cosmeceutical composition, a skin care composition, or a combination thereof.

In some embodiments, the skin barrier restoration therapy comprises administration of a topical composition.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1:
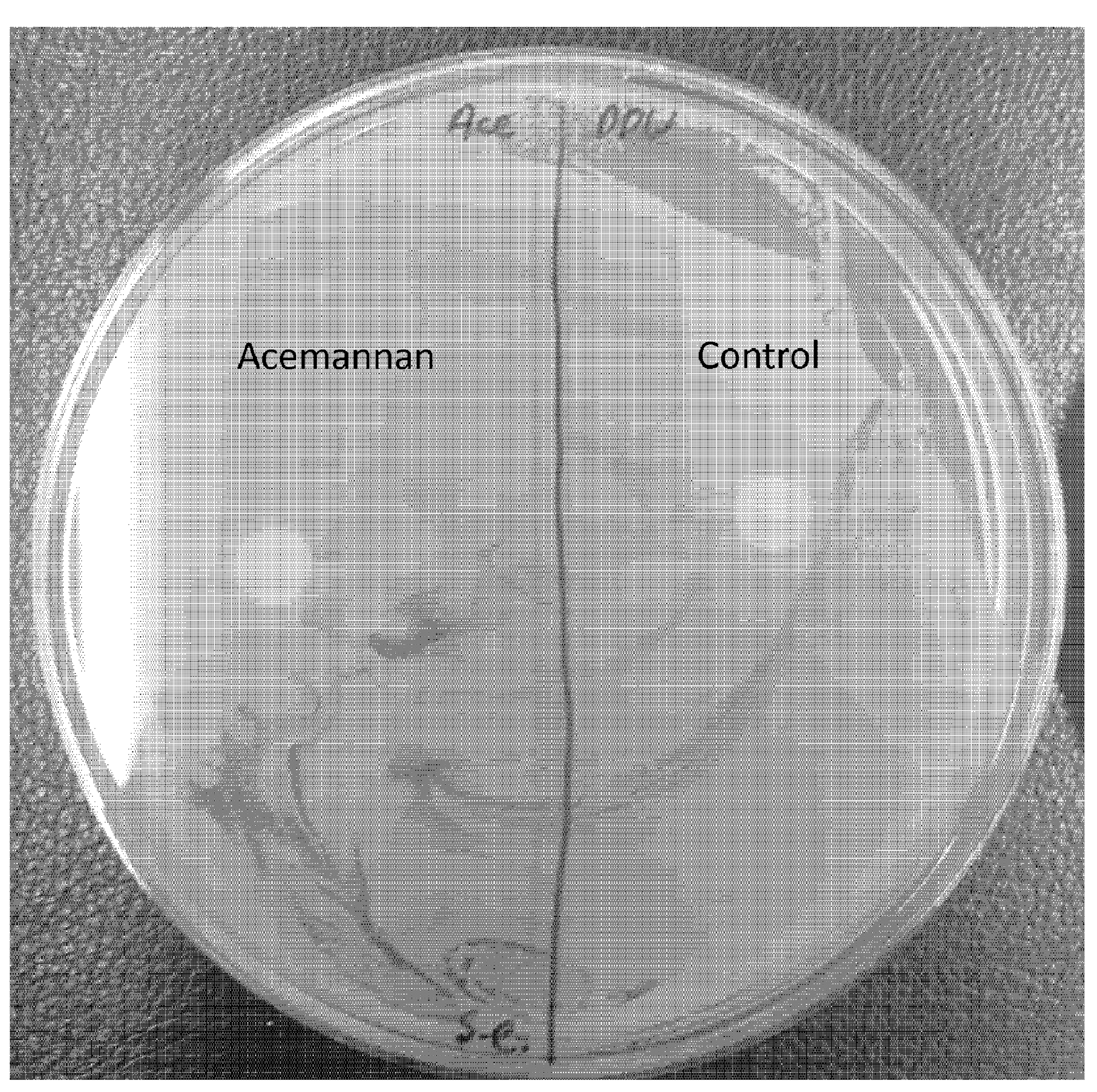
FIG. 1 includes a micrograph of culture plate of *Staphylococcus epidermidis*. The bacteria were cultured on the plate in presence of either Acemannan (0.2% (w/w)) or control (double-distilled water). Comparable levels of bacterial growth were observed on both Acemannan and control.
Figure 2:
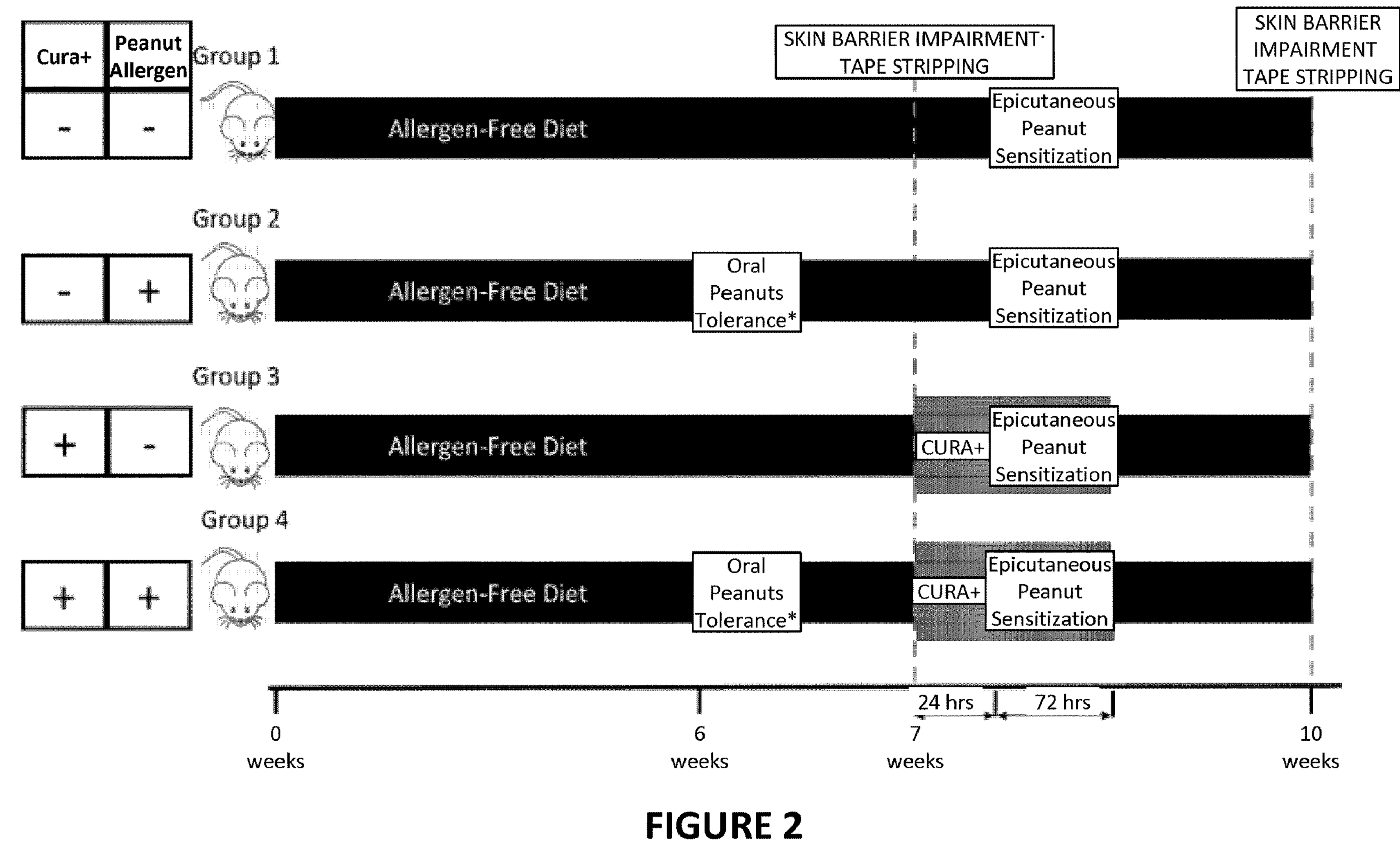
FIG. 2 includes an illustration of a non-limiting scheme of experimental design corresponding with Example 4, as described hereinbelow.

As used herein, the term "IgE-related disease" encompasses and IgE-related disorder. In some embodiments, IgE-related disease comprises any symptom or disorder associated therewith.

Method for Preventing an IgE-Related Disease

According to some embodiments, there is provided a method for selecting and preventing an IgE-related disease in a subject, the method comprising: (a) selecting a subject at a risk of developing an IgE-related disease; and (b) topically administering to the subject a therapeutically effective amount of a composition capable of restoring skin barrier and orally administering to the subject a therapeutically effective amount of a composition comprising an allergen, thereby selecting and preventing an IgE-related disease in a subject.

In some embodiment, a subject being at a risk of developing an IgE-related disease is characterized by or comprises: (i) a TEWL forearm and/or forehead value greater than 7; and (ii) familial history of atopy, food allergy, or both.

In some embodiments, a subject being at a risk of developing an IgE-related disease is further characterized by: (iii) being exposed to pollution.

In some embodiments, the method further comprises a step of determining: (a) trans epidermal water loss (TEWL) of a forearm and/or forehead of the subject; and (b) familial history of atopy, food allergy, or both, of the subject.

In some embodiments, the method further comprises a step of determining: (c) whether the subject is or was exposed to pollution.

In some embodiments, the composition capable of restoring skin barrier comprises a cream, lotion, ointment, or any equivalent thereof.

In some embodiments, the composition capable of restoring skin barrier is a cream.

In some embodiments, the composition capable of restoring skin barrier comprises an immuno-stimulator.

In some embodiments, the composition capable of restoring skin barrier comprises a therapeutically effective amount of acemannan. In some embodiments, acemannan comprises acemannan hydrogel.

In some embodiments, acemannan is present in the first composition in an amount of at least 0.1% (w/w), at least 0.2% (w/w), at least 0.2% (w/w), at least 0.35% (w/w), at least 0.5% (w/w), at least 0.65% (w/w), at least 0.7% (w/w), at least 0.85% (w/w), at least 1.0% (w/w), or any value and range therebetween. Each possibility represents a separate embodiment of the invention.

In some embodiments, acemannan is present in the first composition in an amount ranging from 0.1 to 1.0% (w/w), 0.2 to 1.0% (w/w), 0.3 to 1.0% (w/w), 0.2 to 1.1% (w/w), 0.4 to 0.9% (w/w), or 0.3 to 0.8% (w/w). Each possibility represents a separate embodiment of the invention.

In some embodiments, the composition capable of restoring skin barrier reduces TEWL by at least 5%, 15%, 20%, 35%, 50%, 60%, 75%, 90%, 95%, 99% or 100%, or any value and range therebetween. Each possibility represents a separate embodiment of the invention. In some embodiments, the first composition reduces TEWL by 5-50%, 10-80%, 30-75%, 35-99%, 70-100%, 5-35%, or 40-97%. Each possibility represents a separate embodiment of the invention.

In some embodiments, the composition comprising an allergen is an edible composition. In some embodiments, the composition comprising an allergen comprises a foodstuff.

As used herein, the term "allergen" encompasses any compound or agent acting as an antigen which abnormally triggers the immune system to fights off a perceived threat that would otherwise be harmless.

In some embodiments, allergen comprises a plurality of allergens. In some embodiments, a plurality comprises at least: 2, 3, 5, 7, or 10, or any value and range therebetween. Each possibility represents a separate embodiment of the invention. In some embodiments, a plurality comprises 2-7, 3-5, 4-12, 2-11, or 5-10. Each possibility represents a separate embodiment of the invention.

In some embodiments, the allergen or a composition comprising thereof, comprise a legume, a nut, or any compound derived therefrom.

In some embodiments, the allergen comprises a peanut or a compound derived therefrom.

As used herein, the term "prevention" refers to reducing the susceptibility, delay, prevention, suppression, or inhibition of the onset of a disease, disorder, or condition. As used in accordance with the presently described subject matter, the term "prevention" relates to a process of prophylaxis in which a subject is exposed to the presently described compositions or composition prior to the induction or onset of the disease/disorder process. This could be done where an individual has a genetic pedigree indicating a predisposition toward occurrence of the disease/disorder to be prevented. For example, this might be true of an individual whose ancestors show a predisposition toward certain types of, for example, inflammatory disorders. The term "suppression" is used to describe a condition wherein the disease/disorder process has already begun but obvious symptoms of the condition have yet to be realized. Thus, the cells of an individual may have the disease/disorder, but no outside signs of the disease/disorder have yet been clinically recognized. In either case, the term prophylaxis can be applied to encompass both prevention and suppression. Conversely, the term "treatment" refers to the clinical application of active agents to combat an already existing condition whose clinical presentation has already been realized in a patient.

In some embodiments, preventing comprises reducing the susceptibility of a subject administered with the composition according to the method of the invention, to develop an IgE-related disease. In some embodiments, a subject administered with the composition according to the method of the invention, has reduced susceptibility of developing an IgE-related disease, compared to a control subject. In some embodiments, a control subject is not administered with the composition according to the method of the invention.

Method for Determining Suitability

According to some embodiments, there is provided a method for determining the suitability of a subject for skin barrier restoration therapy, the method comprising: determining (i) trans epidermal water loss (TEWL) of a forearm and/or forehead of the subject; and (ii) familial history of atopy, food allergy, or both, of the subject, wherein: (i) a TEWL forearm and/or forehead value greater than 7; and (ii) familial history of atopy, food allergy, or both, is indicative of suitability of the subject to skin barrier restoration therapy, thereby determining the suitability of a subject for skin barrier restoration therapy.

In some embodiments, the method further comprises determining (iii) whether the subject is or was exposed to pollution.

In some embodiments, exposure to pollution comprises living in an urban area, e.g., a city. In some embodiments, a subject living in an urban area, e.g., a city, is defined herein as being exposed to pollution.

In some embodiments, exposure of the subject to pollution is indicative of suitability of the subject to skin barrier restoration therapy.

In some embodiments, skin barrier restoration therapy comprises administration of a pharmaceutical composition, a cosmeceutical composition, a skin care composition, or a combination thereof.

In some embodiments, skin barrier restoration therapy comprises administration of a topical composition, oral composition, or both.

Prediction Method

In some embodiments, there is provided a method of determining predisposition to developing an immunoglobulin E (IgE)-related disease and/or a disorder associated therewith in a subject, the method comprising calculating a predisposition score based on a plurality of contribution factors.

In some embodiments, the method comprises calculating the predisposition score based on at least one contribution factor selected from parameter group 1 of Table 2 and at least one contribution factor selected from parameter groups 2 to 4 of Table 2; and determining the predisposition of the subject to develop an IgE-related disease according to a predetermined threshold.

As used herein, the term "predisposition" refers to the susceptibility of a subject to a disease, such as an IgE-related disease. In some embodiments, detecting a predisposition comprises detecting the presence of the disease itself. In some embodiments, detecting a predisposition comprises any one of: detecting the risk of developing the disease, determining the susceptibility of the subject to developing the disease, having a poor prognosis for the disease, or any combination thereof. In some embodiments, a subject having a predisposition to a disease is at risk of developing the disease.

In some embodiments, the plurality of contribution factors are assigned to 4 parameter groups, i.e., parameter group 1, parameter group 2, parameter group 3, and parameter group 4 as disclosed hereinbelow in Table 2.

In some embodiments, the plurality of contribution factors comprise positive contribution factors, negative contribution factors, or both.

In some embodiments, parameter groups 1 and 2 of Table 2 comprise positive contribution factors. In some embodiments, parameter groups 3 and 4 of Table 2 comprise negative contribution factors.

As used herein, the term "positive contribution factor" refers to any factor which increases the predisposition to developing an IgE-related disease in the subject, i.e., a risk factor.

As used herein, the term "negative contribution factor" refers to any factor which reduces the predisposition to developing an IgE-related disease in the subject.

In some embodiments, a contribution factor of parameter group 1 of Table 2 is selected from: a Transepidermal water loss (TEWL) value of 13 gr/m$^2$ of at least one of the parents of the subject, a TEWL forearm value of the subject being greater than 7 gr/m$^2$, a TEWL forehead value of the subject being greater than 6.5 gr/m$^2$, and at least one parent of the subject being afflicted with atopy.

As used herein, the term "transepidermal water loss (TEWL)" refers to the loss of water from inside the body through the epidermis to the surrounding environment via diffusion and evaporation. The ability to measure the TEWL is useful in detecting damage to the skin.

In some embodiments, TEWL is measured at the forearm, forehead, inguinal, soles, back, abdomen, palms, or any combination thereof. In some embodiments, the method comprises providing the TEWL values of the subject, a parent of the subject, both parent of the subject, or any combination thereof.

In some embodiments, a TEWL forearm value greater than 7, greater than 7.5, greater than 8, greater than 8.5, or greater than 9, is highly predictive of IgE-related disease. Each possibility represents a separate embodiment of the invention.

In some embodiments, a TEWL forehead value greater than 6, greater than 6.5, greater than 7, greater than 7.5, or greater than 8, is highly predictive of IgE-related disease. Each possibility represents a separate embodiment of the invention.

As used herein, the term "atopy" refers to a predisposition toward developing a certain allergic hypersensitivity reaction. In some embodiments, atopy is genetically inherited, induced by contact with an allergen or an irritant, or both.

In some embodiments, at least one parent of the subject being afflicted with atopy is highly predictive of IgE-related disease to develop in the subject. In some embodiments, having both parents afflicted with atopy increase the predictability of IgE-related disease to develop in the subject compared to having one parent afflicted with atopy.

As used herein, the term "high body fat percentage" comprises body fat percentage measured at birth. In some embodiments, high body fat percentage at birth comprises at least 30% (w/w) per females or at least 24% (w/w) per males, at least 31% (w/w) per females or at least 25% (w/w) per males, at least 32% (w/w) per females or at least 26% (w/w) per males, or at least 33% (w/w) per females or at least 27% (w/w) per males, or any value and range therebetween. Each possibility represents a separate embodiment of the invention. In some embodiments, high body fat percentage at birth comprises 28-32% (w/w) per females or 23-27% (w/w) per males, 29-33% (w/w) per females or 24-28% (w/w) per males, 30-34% (w/w) per females or 25-29% (w/w) per males, or 31-35% (w/w) per females or 26-30% (w/w) per males. Each possibility represents a separate embodiment of the invention.

In some embodiments, a contribution factor of parameter group 2 of Table 2 is selected from: the subject being born in the winter or fall, the subject being born with a body weight of at least 4,000 gr, the subject being exposed to pollution, at least one parent or both parents being exposed to pollution. In one embodiment, the period of exposure of the at least one parent to pollution is prior to or in parallel to the subject being a fetus. In some embodiments, pollution is a rural pollution or an urban pollution.

In some embodiments, being born in the winter or fall increases the predisposition to developing an IgE-related disease in the subject.

In some embodiments, a contribution factor of parameter group 3 of Table 2 is selected from: the subject being exposed to a pet or the subject being exposed to a farm animal.

A pet includes any mammal being reared by humans for social reasons. Non-limiting examples of a pet include, but are not limited to, a cat, a dog, a rabbit, a ferret, a rodent such as a gerbil, a hamster, a chinchilla, a rat, and a guinea pig.

A farm animal includes any mammal or avian being reared by humans for production reasons, i.e., milk, meat, fur, feathers, or any product derived therefrom. Non-limiting examples of a farm animal include, but are not limited to, a donkey, a horse, a mule, a lamb, a duck, a goat, a sheep, a pig, a rooster, a turkey, a goose, a hen, a chicken, and a cow.

In some embodiments, a contribution factor of parameter group 4 of Table 2 is selected from: the subject being a premature infant, or the subject being born with a body weight of 2,500 gr at most.

As used herein, the term "premature infant" or "premature birth" refers to a birth of an infant at fewer than 37 weeks' gestational age.

In some embodiments, the method comprises calculating a predisposition score based on the plurality of contribution factors.

In some embodiments, the calculated predisposition score is based on the scores of: at least one contribution factor selected from the parameter group 1 of Table 2 and at least one contribution factor selected from the parameter group 2 of Table 2.

In some embodiments, the calculated predisposition score is based on the scores of: at least one contribution factor selected from the parameter group 1 of Table 2 and at least one contribution factor selected from the parameter group 3 of Table 2.

In some embodiments, the calculated predisposition score is based on the scores of: at least one contribution factor selected from the parameter group 1 of Table 2 and at least one contribution factor selected from the parameter group 4 of Table 2.

In some embodiments, the calculated predisposition score is based on the scores of: at least one contribution factor selected from the parameter group 1 of Table 2, at least one contribution factor selected from the parameter group 2 of Table 2, and at least one contribution factor selected from the parameter group 3 of Table 2.

In some embodiments, the calculated predisposition score is based on the scores of: at least one contribution factor selected from the parameter group 1 of Table 2, at least one contribution factor selected from the parameter group 2 of Table 2, and at least one contribution factor selected from the parameter group 4 of Table 2.

In some embodiments, the calculated predisposition score is based on the scores of: at least one contribution factor selected from the parameter group 1 of Table 2, at least one contribution factor selected from the parameter group 2 of Table 2, at least one contribution factor selected from the parameter group 3 of Table 2, and at least one contribution factor selected from the parameter group 4 of Table 2.

In some embodiments, the subject is an infant.

The terms "infant", "baby", "preemie", "newborn", are used herein interchangeably.

In some embodiments, the subject is 1 week old at most, 2 weeks old at most, 3 weeks old at most, 4 weeks old at most, 5 weeks old at most, 1 month old at most, 2 months old at most, 3 months old at most, 4 months old at most, 6 months old at most, 8 months old at most, or 12 months old at most, or any value and range therebetween. Each possibility represents a separate embodiment of the invention.

In some embodiments, the subject is 1~4 weeks old, 2-5 weeks old, 3-6 weeks old, 3 weeks to 2 months old, 1 week to 3 months old, 4 weeks to 5 months old, 2 weeks to 10 months old, or 1 week to 12 months old. Each possibility represents a separate embodiment of the invention.

In some embodiments, the subject is a fetus.

As used herein, the term "fetus" refers to any unborn offspring of an animal which has developed from an embryo.

Following hereinbelow is a non-limiting table including a plurality of contribution factors of IgE-related diseases.

TABLE 1

| contribution factors<br>Contribution factor |
|---|
| Single parent with TEWL value of 13 $gr/m^2$ |
| Both parent with TEWL value of 13 $gr/m^2$ |
| Subject TEWL forearm > 9 $gr/m^2$ |
| 7 $gr/m^2$ < Subject TEWL forearm < 9 $gr/m^2$ |
| Subject TEWL forehead > 6.5 $gr/m^2$ |
| Single parent with atopy |
| Both parents with atopy |
| Subject born with a body weight of at least 4,000 gr |
| Subject born in winter or fall |
| Subject being exposed to pollution |
| At least one parent being exposed to pollution |
| Subject exposed to a pet |
| Subject exposed to a farm animal |
| Subject born preterm |
| Subject born with a body weight of 2,500 gr at most |

In some embodiments, the method comprises calculating a predisposition score based on a plurality of contribution factors. In some embodiments, the method comprises calculating a predisposition score based on a plurality of contribution factors selected from table 1.

In some embodiments, a plurality is at least 2, at least 3, at least 4, at least 5, at least 6, at least 7, at least 8, at least 9, or at least 10 contribution factors, or any value and range therebetween. Each possibility represents a separate embodiment of the invention.

In some embodiments, a plurality is 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10 contribution factors. Each possibility represents a separate embodiment of the invention.

Following hereinbelow is a non-limiting table, comprising scores of the aforementioned contribution factors.

TABLE 2 contribution factors and respective scores

| Parameter group | Contribution factor | Score |
|---|---|---|
| 1 | Single parent with TEWL value of 13 gr/m$^2$ | 10-15 |
| | Both parent with TEWL value of 13 gr/m$^2$ | 20-30 |
| | Subject TEWL forearm > 9 gr/m$^2$ | 21-27 |
| | 7 gr/m$^2$ < Subject TEWL forearm < 9 gr/m$^2$ | 13-17 |
| | Subject TEWL forehead > 6.5 gr/m$^2$ | 5-7 |
| | Single parent with atopy | 11-15 |
| | Both parents with atopy | 25-31 |
| | Subject born with a body weight of at least 4,000 gr | 10-12 |
| 2 | Subject born in winter or fall | 2-4 |
| | Subject being exposed to pollution | 1-3 |
| | At least one parent of the subject being exposed to pollution | 1-3 |
| | Black or Asian skin type/origin | 1-5 |
| | Subject being the first child | 1-3 |
| | Mother over the age of 38 at subject's birth | 2-5 |
| | Subject being born in a C-section type of birth | 1-4 |
| | Maternal smoking during pregnancy of the subject | 2-4 |
| | Household smoker after birth of the subject | 1-3 |
| | No planned or lack of vitamin D supplementation | 3-5 |
| | Systemic antibiotics in first 3 months of subject's life | 1-3 |
| 3 | Subject exposed to a pet | (−6)-(−8) |
| | Subject exposed to a farm animal | (−10)-(−12) |
| | First neonatal bath after more than 12 hr post birth | (−3)-(−5) |
| 4 | Subject born preterm | (−1)-(−3) |
| | Subject born with a body weight of 2,500 gr at most | (−5)-(−7) |
| | Subject being a third or more | (−3)-(−5) |
| | Subject being breast fed | (−2)-(−4) |
| | Subject attended day care from the age of 1 to 6 months old | (−2)-(−4) |
| | Subject often being supplemented with probiotics | (−3)-(−5) |

Following hereinbelow is a non-limiting table presenting assignment to risk categories based on the calculated score, as specified in the Table 2.

TABLE 3

Calculated scores and classification to risk categories

| Calculated score | Risk Category |
|---|---|
| 0-7 | Low risk |
| 8-29 | Moderate risk |
| 30-53 | High risk |
| 54-70 | Very high risk |

In some embodiments, the herein disclosed calculated predisposition score provides the determining of the predisposition of the subject to develop an IgE-related disease with an increased prediction sensitivity, compared to a control prediction.

In some embodiments, a control prediction comprises any prediction not including at least one contribution factor selected from parameter group 1.

In some embodiment, a predetermined threshold is a control as specified hereinabove. In some embodiments, a predetermined threshold is the score of a healthy subject. In some embodiments, a predetermined threshold is equivalent to the score that a healthy subject obtains or is reflected by. In some embodiments, a predetermined threshold is the average score of a healthy population. In some embodiments, a predetermined threshold is equivalent to the score that a healthy population obtains or is reflected by.

In some embodiments, increased sensitivity is by at least 5%, at least 25%, at least 50%, at least 100%, at least 250%, at least 350%, at least 500%, at least 750%, or at least 1,000% more sensitive compared to control, or any value and range therebetween. Each possibility represents a separate embodiment of the invention.

In some embodiments, increased sensitivity is by 5-75%, 50-250%, 100-350%, 300-550%, 400-750%, or 700-1,000% more sensitive compared to control. Each possibility represents a separate embodiment of the invention.

In some embodiments, an IgE-related disease is selected from: atopic dermatitis, allergic asthma, allergic rhinitis, food allergy, eczema, lupus, rheumatoid arthritis, psoriasis, psoriasis vulgaris, acne, acne vulgaris, rosacea, skin and soft tissue infections, dandruff, blepharitis, tinea versicolor, or a combination thereof.

In some embodiments, an IgE-related disease is atopic dermatitis.

In some embodiments, an IgE-related disease comprises increased amounts of primed basophils, primed mast cells, or both.

In some embodiments, the subject is characterized by having increased amounts of primed basophils, primed mast cells, or both.

In some embodiments, a subject afflicted with an IgE-related disease is characterized by having increased amounts of primed basophils, primed mast cells, or both.

In some embodiments, a method for preventing an IgE-related disease in a subject, the method comprising: determining whether the subject is at a moderate risk to a very high risk of developing an IgE-related disease according to the herein disclose method; and topically administering to the subject determined being at a moderate to a very high risk a pharmaceutical or a cosmeceutical composition, is provided.

In some embodiments, determining the predisposition to developing an IgE-related disease in the subject is performed no later than the subject being 1 week old, being 2 weeks old, being 3 weeks old, being 1 month old, being 2 months old, or being 3 months old, or any value and range therebetween. Each possibility represents a separate embodiment of the invention.

In some embodiments, preventing comprises reducing the disease severity, delaying the disease onset, reducing the disease cumulative incidence, or any combination thereof.

In some embodiments, the method comprises calculating a predisposition of the subject to develop a food allergy based on a plurality of contribution factors. In some embodiments, the method comprises calculating a predisposition score based on a plurality of contribution factors selected from table 4.

TABLE 4

| food allergy contribution factors and respective scores<br>Contribution factor |
|---|
| Birthweight (Large for gestational age (LGA) or non-LGA) |
| Apgar score |
| Season of birth |
| Cesarean section delivery |
| Gestational age |
| Gender |
| Ethnicity |
| Maternal atopic dermatitis |
| Number of older siblings |
| Familial history |
| Maternal seasonal allergy |
| TEWL |
| Pets in household |
| Rural and Urban communities |
| Attending a day care |
| Vitamin D supplementation |
| Exclusively breastfed |

Following hereinbelow is a non-limiting table, comprising scores of the aforementioned food allergy contribution factors.

TABLE 5 contribution factors and respective scores

| Parameter group | Contribution factor | Score |
|---|---|---|
| 1 | TEWL forearm > 9 gr/m$^2$ | 18-22 |
| | 7 gr/m$^2$ < TEWL forearm < 9 gr/m$^2$ | 7-9 |
| | Familial food allergy in 2 or more members | 9-12 |
| | Maternal atopic dermatitis | 7-9 |
| | One or both parents of Asian origin | 6-8 |
| | Maternal age > 30 years | 8-10 |
| | Sibling seasonal allergies | 7-9 |
| | Maternal seasonal allergies | 6-8 |
| 2 | 7 gr/m$^2$ > TEWL forehead > 5 gr/m$^2$ | 4-5 |
| | Familial food allergy in 1 member | 3-5 |
| | Subject born in the fall/winter | 2-4 |
| | Apgar score < 7 | 1-3 |
| | Birthweight-LGA | 1-2 |
| | Cesarean section delivery | 1-2 |
| | Subject is a male | 2-4 |
| | Subject is born to a rural community | 1-3 |
| | Subject is exclusively breastfed | 1-3 |
| 3 | Subject is supplemented with Vitamin D | (−4)-(−6) |
| | Subject is a third child | (−3)-(−5) |
| | Subject is a second child | (−1)-(−2) |
| | Subject exposed to a pet (e.g., a dog) at <5 years | (−3)-(−5) |
| | Subject is attending a day care | (−1)-(−2) |
| | Gestational age-prior to 37 weeks | (−1)-(−2) |

Following hereinbelow is a non-limiting table presenting assignment to risk categories for developing a food allergy, based on the calculated score, as specified in the Table 5.

TABLE 6

Calculated scores and classification to food allergy risk categories

| Calculated score | Risk Category |
|---|---|
| 0-19 | Low risk |
| 20-24 | Moderate risk |
| 25-47 | High risk |
| 48-100 | Very high risk |

In some embodiments, the method of the invention comprises topically administering a therapeutic composition, such as a cream, e.g., comprising acemannan, to at least one parent of the subject so as to prevent an IgE-related disease in the subject. In some embodiments, preventing an IgE-related disease in a subject comprises administering a therapeutic composition, such as a cream, e.g., comprising acemannan, to at least one parent of the subject, while the subject is a fetus. In some embodiments, preventing an IgE-related disease in a subject comprises administering a therapeutic composition, such as a cream, e.g., comprising acemannan, to a pregnant woman. In some, preventing an IgE-related disease in a subject comprises administering a therapeutic composition, such as a cream, e.g., comprising acemannan, to a pregnant woman forecasted to undergo caesarian section. In some embodiments, according to the herein disclosed method, a pregnant woman forecasted to undergo a caesarian section is topically administered with the therapeutic composition at least 1 week, at least 2 weeks, at least 4, at least 6 weeks, at least 1 month, at least 2 months, at least 3 months, at least 4 months, at least 5 months, at least 6 months, at least 7 months, or at least 8 months before the forecasted caesarian section, or any value and range therebetween. Each possibility represents a separate embodiment of the invention. In some embodiments, according to the herein disclosed method, a pregnant woman forecasted to undergo a caesarian section is topically administered with the therapeutic composition 1 to 3 weeks, 2 to 9 weeks, 4 to 12 weeks, 6 to 18 weeks, 1 to 4 months, 2 to 6 months, 3 to 7 months, 4 to 6 months, 5 to 8 months, or 1 to 8 months before the forecasted caesarian section. Each possibility represents a separate embodiment of the invention.

In some embodiments, both parents of the subject are topically administered with a therapeutic composition, such as a cream, e.g., comprising acemannan, so as to prevent an IgE-related disease in the subject.

In some embodiments, an IgE-related disease as described above, relates to or correlates with the skin microbiome of the subject. In some embodiments, a healthy subject comprises a healthy skin microbiome whereas a subject afflicted with an IgE-related disease comprises an unhealthy skin microbiome. In some embodiments, the skin microbiome changes, being altered, or modified in an IgE-related disease afflicted subject compared to a healthy subject.

In some embodiments, modifying or altering the skin microbiome of a subject afflicted with IgE-related disease so as to resemble the microbiome of a healthy subject, may provide treatment or prevention of the IgE-related disease, or reduce or alleviate a symptom thereof.

In one embodiment, the present invention provides a method of suppressing, inhibiting, or proactively treating an IgE-related disease, disorder, or condition in a subject comprising the steps of: a) analyzing the microbiome on the skin of the subject; and b) administering a pharmaceutical composition for modifying the skin microbiome if a microbiome indicative of increased likelihood to develop the IgE-related disease, disorder, or condition is detected. In another embodiment, the present invention provides a method of suppressing, inhibiting, or proactively treating an IgE-related disease, disorder, or condition in a subject comprising the steps of: a) analyzing the microbiome on the skin of the subject; and b) administering a pharmaceutical composition for modifying the skin microbiome if a microbiome indicative of increased likelihood to develop the skin disease, disorder, or condition is detected.

In one embodiment, the microbiome indicative of increased likelihood to develop an IgE-related disease, disorder, or condition comprises reduced bacterial community diversity. In another embodiment, the microbiome indicative of increased likelihood to develop the IgE-related disease, disorder, or condition comprises *Staphylococcus aureus* colonization. In another embodiment, the microbiome indicative of increased likelihood to develop the IgE-related disease, disorder, or condition comprises high *S. aureus* colonization. In another embodiment, the microbiome indicative of increased likelihood to develop the IgE-related disease, disorder, or condition comprises reduced *S. epidermidis*, reduced *S. hominis* colonization, increased *Corynebacterium* colonization, or a combination thereof.

In another embodiment, the present invention provides a method of suppressing, inhibiting, or proactively treating an IgE-related disease, disorder, or condition in a subject comprising the steps of: a) detecting a pathological microbiome on the skin of the subject; and b) administering a pharmaceutical composition for modifying the skin microbiome to the subject.

In one embodiment, the phrase "pathological microbiome" as used herein refers to a microbiome derived from a subject who is known to have a disease (i.e., IgE-related disease, for example atopic dermatitis) or from a subject who is known to have later developed the disease.

In another embodiment, the present invention provides a method of suppressing, inhibiting, or proactively treating an IgE-related disease, disorder, or condition in a subject comprising the steps of: a) detecting *Staphylococcus* colonization on the skin of the subject; and b) administering a pharmaceutical composition for modifying the skin microbiome to the subject.

In one embodiment, the step of detecting *Staphylococcus* colonization comprises detecting *S. aureus, S. epidermidis, S. hominis*, or a combination thereof. In one embodiment, if high levels of *S. aureus* are detected, the pharmaceutical composition is administered. In one embodiment, if low levels of *S. epidermidis, S. hominis*, or both, are detected, the pharmaceutical composition is administered. In one embodiment, the step of detecting *Staphylococcus* colonization on the skin of the subject comprises identification of a specific nucleotide sequence unique to cutaneous associated *S. aureus* species via PCR amplification of a gene fragment by gene-specific PCR primers.

In one embodiment, a subject as described herein lacks a diagnosis of the IgE-related condition, symptoms of the skin condition, or a combination thereof.

In one embodiment, the skin which is analyzed is a portion of the skin that comprises a signature IgE-related disease microbiome. In one embodiment, the skin site comprises the antecubital fossa, popliteal fossae, axillary fossa, nasal tip, cheek, dorsal forearm, volar forearm, or a combination thereof.

In another embodiment, the skin site comprises the nare, glabella, axillary vault, interdigital web space, inguinal crease, gluteal crease, plantar heel, umbilicus, or a combination thereof.

In another embodiment, the skin comprises the glabella, alar crease, external auditory canal, manubrium, hypothenar palm, toe web space, retroauricular crease, occiput, back, buttock, or a combination thereof.

In one embodiment, the skin of the subject is analyzed in situ. In another embodiment, the skin of the subject is analyzed in a sample taken from the skin of the subject. In one embodiment, the sample is analyzed in vitro, which, in one embodiment, is in culture. In one embodiment, one or more samples are collected via swabbing, scraping, biopsy, or a combination thereof.

Microbiome Analysis

In one embodiment, the step of analyzing the microbiome comprises culturing the skin sample from the subject on selective agar. In one embodiment, the selective agar is chromagar. In another embodiment, the step of analyzing the microbiome comprises nucleotide sequencing of the skin sample from the subject for bacterial nucleotide sequences. In one embodiment, the nucleotide sequencing comprises sequencing of the gene encoding the 16S ribosomal RNA (16S rRNA).

In another embodiment, analyzing the microbiome in the sample comprises 16S rRNA gene sequencing or whole genome shotgun metagenomics. In one embodiment, the nucleotide sequencing comprises DNA sequencing.

In another embodiment, the step of analyzing the microbiome comprises identification of a specific nucleotide sequence via PCR amplification of a gene fragment by gene-specific PCR primers. In another embodiment, the step of analyzing the microbiome comprises detection of volatile metabolites. In one embodiment, the volatile metabolites are detected by gas chromatography-mass spectrometry (GC-MS) screen or an electronic nose. In one embodiment, the volatile metabolites comprise aldehydes. In one embodiment, the aldehydes comprise acetaldehyde, 3-methylbutanal, or a combination thereof. In another embodiment, the volatile metabolites comprise acids, ketones, hydrocarbons, alcohols, esters, volatile sulfur compounds (VSCs), volatile nitrogen compounds (VNCs), or a combination thereof. In one embodiment, the acids comprise isovaleric acid, said ketones comprise acetoin or 2-nonanone. In one embodiment, the hydrocarbons comprise 2-butene, 1,10-undecadiene. In one embodiment, the alcohols comprise 2-methyl-1-propanol or 2-butanol. In one embodiment, the esters comprise ethyl formate or methyl 2-methylbutyrate. In one embodiment, the VSCs comprise dimethylsulfide. In one embodiment, the VNCs comprise 3-methylpyrrole.

In one embodiment, the microbiome is analyzed using hyperspectral imaging, which, in one embodiment, comprises pushbroom, acouto-optic tunable filter (AOTF), filter wheel, or liquid crystal tunable filter (LCTF) hyperspectral imaging.

In another embodiment, the step of analyzing the microbiome comprises an optical detection technique, an electrochemical detection technique, or a mass detection technique.

In embodiments, methods are provided which comprise, inter alia, collecting a biological sample from skin of a subject and analyzing the microbiome in the sample. Modern techniques for skin microbial analysis are known and within the understanding of the ordinarily skilled artisan and specific methods and techniques can be employed and adjusted to best suit the aims of the study.

In general, several procedural practices should be considered before the study begins, including avoiding contamination by environmental DNA, storage in warm conditions, and the exposure of the samples to researchers and clinicians. Further, precautions should be taken to ensure a sterile technique is utilized, and that bacterial DNA sequences (not only live bacterial organisms) are not introduced into the sample from sampling equipment, lab reagents, and clinicians.

To obtain samples, microorganisms from the skin can be collected by any suitable method known in the art, including, without limitation, swabbing, scraping or collecting biopsies using sterile techniques. Skin samples can be collected from any suitable location, including, without limitation, the nare, axillary vault, antecubital fossa, interdigital webspace, inguinal crease, gluteal crease, popliteal fossa, plantar heel, umbilicus, or a combination thereof. Appropriate and effective sample storage conditions should also be employed. If sterile sample collection is combined with effective storage conditions, an accurate representation of the skin microbiome should be maintained prior to DNA extraction and analysis. Once the samples are obtained and properly stored, DNA extractions can then be performed. Several different methods have been developed for the extraction of skin microbiome samples, including the REPLI-g Midi kit (Qiagen, Limberg, The Netherlands), Qiagen DNA Extraction Kit (Qiagen), and DNeasy DNA Extraction kit (Qiagen). In an effort to obtain the most accurate representation of the microbial diversity, studies have also explored different kit and non-kit based extraction methods, such as disruption of bacterial cell walls (e.g., bead beating or enzymatic lysis).

After DNA extraction, the specific target species or classes of microorganisms need to be identified to determine the most appropriate sequencing strategy. For example, bacterial communities can be assessed by amplifying a variable region of the conserved 16S ribosomal RNA gene, while fungal species can be targeted by applying 18S ribosomal RNA gene or the internal transcribed spacer.

While culturing methods can be used in detecting bacterial strains in accordance with embodiments described herein, targeted sequencing approaches do not require any culturing methods and hundreds of samples can be analyzed on a single sequencing run, providing an efficient and cost-effective means to examining microbial communities. Alternatively, shotgun sequencing can be performed, which will identify a subset of random DNA sequences from the sample. In either approach, sequencing technologies should also be taken into account. While Roche 454 or Illumina MiSeqs can provide adequate sequencing coverage or depth for targeted amplicon sequencing, deeper coverage attainable through Illumina HiSeq or Pacific Biosciences technologies may be better suited for shotgun sequencing.

16S data processing—The 16S sequence data can be processed in accordance with any suitable techniques known to one of skill in the art, including as previously described (McDonald, et al., 2018). In one embodiment, processing can use a sequence variant method, such as Deblur v1.0.2, trimming to 125 nucleotides, to maximize the specificity of 16S data. Following processing by Deblur, previously recognized bloom sequences can be removed. The Deblur sOTUs can be inserted into the Greengenes 13_8 (19) 99% reference tree using SEPP. SEPP uses the simultaneous alignment and tree estimation strategy as previously described (Liu et al., 2009) to identify reasonable placements for sequence fragments within an existing phylogeny and alignment. Taxonomy can be assigned using an implementation of the RDP classifier as implemented in QIIME2. (McDonald, et al.).

Principal coordinates analysis can be undertaken in accordance with any suitable techniques known to one of skill in the art. In one embodiment, a distance matrix can be constructed using, for example, without limitation, the Bray Curtis dissimilarity index. In an embodiment, principal coordinates analyses can be implemented using, for example, without limitation, EMPeror software.

Bacterial Strains

In some embodiments, a vast number of bacterial strains potentially present in the skin microbiome can be detected and analyzed, and information obtained therefrom used in accordance with the methods and various techniques described herein.

In one embodiment, bacterial strains detected in a skin sample obtained in accordance with methods described herein comprise, without limitation, *Acidaminococcus, Acinetobacter, Actinomyces, Actinomyces, Aerococcus, Anaerococcus, Arcanobacterium, Atopobium, Atopobium vaginae, Bacteroides ovatus, Bacteroides uniformis, Brevibacillus, Brevibacterium paucivorans, Campylobacter ureolyticus, Cellvibrio, Citrullus lanatus, Coprococcus, Corallococcus exiguus, Corynebacterium, Corynebacterium kroppenstedtii, Dermabacter, Dialister, Enhydrobacter, Facklamia, Faecalibacterium prausnitzii, Finegoldia, Flavobacterium, Gallicola, Gardnerella, Gemella*, GW-34, *Haemophilus, Moryella indoligenes, Parabacteroides, Parvimonas, Peptococcus, Peptoniphilus*, ph2, *Porphyromonas, Prevotella, Providencia, Pseudoclavibacter bifida, Pseudomonas, Pseudonocardia, Rhodobacter, Rickettsiella, Roseburia, Roseburia faecis, Ruminococcus, Scardovia, Shuttleworthia, Sneathia, Sneathia, Sphingomonas, Streptococcus anginosus, Streptococcus, Streptococcus sobrinus, Thermoactinomyces, Wautersiella*, or any combination thereof.

In another embodiment, bacterial strains detected in a skin sample obtained in accordance with methods described herein can comprise, without limitation, *Bacillus cereus, Blastomonas, Chryseobacterium, Comamonas, Erythromicrobium, Fusobacterium, Gardnerella, Haemophilus parainfluenzae, Paracoccus, Phenylobacterium, Prevotella, Prevotella copri, Sphingobium yanoikuae, Stenotrophomonas, Streptococcus, Streptococcus infantis, Vagococcus*, or any combination thereof. In one embodiment, the strains can be detected in a healthy subject.

In one embodiment, bacterial strains detected in a skin sample obtained in accordance with methods described herein can comprise one or more of the four dominant phyla of bacteria residing on the skin, which in one embodiment, comprise the Actinobacteria, Proteobacteria, Firmicutes, and Bacteroidetes.

In one embodiment, the presence of microbial strains in a subject that are also present in a subjects that is currently afflicted with an IgE-related disease, such as atopic dermatitis, or in a subject that is predicted to develop atopic dermatitis, is predictive of the onset of atopic dermatitis. Conversely, the absence of microbial strains in a subject that are absent in a subject that is currently afflicted with an IgE-related disease, such as atopic dermatitis, or in a subject that is predicted to develop atopic dermatitis, is predictive of the onset of atopic dermatitis.

In another embodiment, high levels of microbial strains in a subject that are enriched in a subject that is currently afflicted with an IgE-related disease, such as atopic dermatitis, or in a subject that is predicted to develop atopic dermatitis, is predictive of the onset of atopic dermatitis.

Conversely, low levels of microbial strains in a subject that are in low levels in a subject that is currently afflicted with an IgE-related disease, such as atopic dermatitis, or in a subject that is predicted to develop atopic dermatitis, is predictive of the onset of atopic dermatitis.

In another embodiment, the presence or high levels of microbial strains in a subject that are absent or at low levels in a subject that is not afflicted with an IgE-related disease, such as atopic dermatitis, or in a subject that is not predicted to develop atopic dermatitis, is predictive of the onset of atopic dermatitis. Conversely, the absence or low levels of microbial strains in a subject that are present or enriched in a subject that is not afflicted with an IgE-related disease, such as atopic dermatitis, or in a subject that is not predicted to develop atopic dermatitis, is predictive of the onset of atopic dermatitis.

In another embodiment, the presence of bacterial strains in a given subject that are also present in a subject that is afflicted with an IgE-related disease, such as atopic dermatitis is diagnostic of atopic dermatitis. In another embodiment, the absence of bacterial strains in a given subject that are absent in a subjects that is afflicted with an IgE-related disease, such as atopic dermatitis is diagnostic of atopic dermatitis. In another embodiment, high levels of bacterial strains in a given subject that are also present in high levels in a subject that is afflicted with an IgE-related disease, such as atopic dermatitis is diagnostic of atopic dermatitis. In another embodiment, low levels of bacterial strains in a given subject that are at low levels in a subject that is afflicted with an IgE-related disease, such as atopic dermatitis is diagnostic of atopic dermatitis.

In another embodiment, the presence or high levels of bacterial strains in a given subject that are absent or at low levels in a subject is not afflicted with an IgE-related disease, such as atopic dermatitis is diagnostic of atopic dermatitis. In another embodiment, the absence or low levels of bacterial strains in a given subject that are present or at high levels in a subject that is not afflicted with an IgE-related disease, such as atopic dermatitis is diagnostic of atopic dermatitis.

Composition

In one embodiment, the present invention provides methods comprising the step of administering a pharmaceutical or a cosmeceutical composition. As used herein, the terms "pharmaceutical" and "cosmeceutical" are interchangeable.

In one embodiment, the pharmaceutical composition is in the form of an oil, a lotion, a cream, or an ointment. In some embodiments, the pharmaceutical composition is an emulsion. In some embodiments, an emulsion is selected from a single emulsion, a double emulsion, a water in oil emulsion, an oil in water emulsion, a water in oil in water emulsion, an oil in water in oil emulsion, a micro emulsion, a nano emulsion, or any combination thereof. In one embodiment, the pharmaceutical composition alters nutrient availability on the skin of the subject. In one embodiment, the pharmaceutical composition comprises nutrients that enhance bacterial growth. In one embodiment the nutrients are prebiotics, which in one embodiment comprise fructans, galactans, or a combination thereof. In another embodiment, the pharmaceutical composition comprises probiotics, which, in one embodiment, comprise *Bifidobacterium, Brevibacterium, Propionibacterium, Lactococcus, Streptococcus, Lactobacillus* (e.g., *L. acidophilus*), *Enterococcus, Pediococcus, Leuconostoc*, Oenococcus, or a combination thereof.

In one embodiment, the pharmaceutical composition alters skin metabolites. In another embodiment, the pharmaceutical composition decreases *S. aureus*, increases *S. epidermidis*, increases *S. homonis*, decreases *Corynebacterium* colonization, or a combination thereof.

The amount of the pharmaceutical composition that is administered and the dosage regimen for treating a disease condition with the compositions of this invention depends on a variety of factors, including the age, weight, gender, the medical condition of the subject, the type of disease, the severity of the disease, the route and frequency of administration, and the particular compound employed. Thus, the dosage regimen may vary widely, but can be determined routinely using standard methods. The daily dose can be administered in one to four doses per day.

The pharmaceutical composition can be administered by any means suitable for the condition to be treated, which can depend on the need for site-specific treatment or quantity of the pharmaceutical composition to be delivered. The compositions of the present invention may, for example, be administered orally, mucosally, transmucosally, transdermally, intra-dermally, or parentally including intravascularly, intravenously, intraperitoneally, subcutaneously, intramuscularly, intra-ventricularly, or intrasternally. In one embodiment, the pharmaceutical composition is administered topically.

In another embodiment, the pharmaceutical compositions are administered topically to body surfaces and are thus formulated in a form suitable for topical administration. Suitable topical formulations include gels, ointments, creams, lotions, drops and the like. For topical administration, the therapeutic agent is prepared and applied as a solution, suspension, or emulsion in a physiologically acceptable diluent with or without a pharmaceutical carrier.

In another embodiment, the pharmaceutical compositions provided herein are controlled-release compositions, i.e. compositions in which the therapeutic agent is released over a period of time after administration. Controlled- or sustained-release compositions include formulation in lipophilic depots (e.g. fatty acids, waxes, oils). In another embodiment, the composition is an immediate-release composition, i.e. a composition in which all of the therapeutic agent is released immediately after administration.

Another formulation suitable for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

In one embodiment, the compositions are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

It may be desirable to administer a pharmaceutical composition of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material. According to some embodiments, administration can be by direct injection e.g., via a syringe.

Effective doses of the compositions of the present invention, for treatment of conditions or diseases vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy. The pharmaceutical compositions of the invention thus may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

Furthermore, a skilled artisan would appreciate that the term "therapeutically effective amount" may encompass total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of a compound of the invention that will be effective in the treatment of a particular disorder or condition, including an inflammatory-associated disease, also will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. In one embodiment, the dosage will be within the range of 0.01-1000 mg/kg of body weight. In another embodiment, the dosage will be within the range of 0.1 mg/kg to 100 mg/kg. In another embodiment, the dosage will be within the range of 1 mg/kg to 10 mg/kg. Effective doses may be extrapolated from dose-response curves derived from in vitro or animal model test bioassays or systems.

For therapeutic purposes, the active compounds of this invention are ordinarily combined with one or more adjuvants appropriate to the indicated route of administration.

Pharmaceutical compositions of this invention optionally comprise an additional agent selected from any pharmaceutically acceptable carrier, adjuvant, and vehicle.

In one embodiment, a subject as described herein is an infant. In one embodiment, the infant is at least 2 weeks old. In another embodiment, the infant is approximately 3 months old. In another embodiment, the subject is a child. In another embodiment, the subject is an adult.

Timing and Site of Administration

In some embodiments, a composition is administered on at least one day, at least two days, at least three days, at least four days, at least five days, at least six days, at least seven days, at least eight days, at least nine days, at least ten days, at least eleven days, at least twelve days, at least 13 days, at least 14 days, at least 21 days, or all 28 days of a 28 day treatment cycle. In particular embodiments, a composition is administered to a subject once a day. In other particular embodiments, a composition is administered twice a day. In certain embodiments a composition is administered more than twice a day.

In one embodiment, one or more of the compositions as described herein are administered once per day. In another embodiment, one or more of the compositions as described herein are administered twice per day. In another embodiment, one or more of the compositions as described herein are administered three times per day. In another embodiment, one or more of the compositions as described herein are administered four times per day. In another embodiment, one or more of the compositions as described herein are administered once every two days, once every three days, twice a week, once a week, once every 2 weeks, once every 3 weeks.

In one embodiment, one or more of the compositions as described herein are administered for 7 days to 28 days. In another embodiment, one or more of the compositions as described herein are administered for 7 days to 8 weeks. In another embodiment, one or more of the compositions as described herein are administered for 7 days to 50 days. In another embodiment, one or more of the compositions as described herein are administered for 7 days to six months. In another embodiment, one or more of the compositions as described herein are administered for 7 days to one and half years. In another embodiment, one or more of the compositions as described herein are administered for 14 days to 12 months. In another embodiment, one or more of the compositions as described herein are administered for 14 days to 3 years. In another embodiment, one or more of the compositions as described herein are administered for several years. In another embodiment, one or more of the compositions as described herein are administered for one month to six months.

In one embodiment, one or more of the compositions as described herein are administered for 7 days. In another embodiment, one or more of the compositions as described herein are administered for 14 days. In another embodiment, one or more of the compositions as described herein are administered for 21 days. In another embodiment, one or more of the compositions as described herein are administered for 28 days. In another embodiment, one or more of the compositions as described herein are administered for 50 days. In another embodiment, one or more of the compositions as described herein are administered for 56 days. In another embodiment, one or more of the compositions as described herein are administered for 84 days. In another embodiment, one or more of the compositions as described herein are administered for 90 days. In another embodiment, one or more of the compositions as described herein are administered for 120 days.

The number of times a composition is administered to a subject in need thereof depends on the discretion of a medical professional, the disorder, the severity of the disorder, and the subject's response to the formulation. In some embodiments, a composition disclosed herein is administered once to a subject in need thereof with a mild acute condition. In some embodiments, a composition disclosed herein is administered more than once to a subject in need thereof with a moderate or severe acute condition. In the case wherein the subject's condition does not improve, upon the doctor's discretion the composition may be administered chronically, that is, for an extended period of time, including throughout the duration of the subject's life in order to ameliorate or otherwise control or limit the symptoms of the subject's disease or condition.

In the case wherein the subject's status does improve, upon the doctor's discretion the composition may administered continuously; or, the dose of drug being administered may be temporarily reduced or temporarily suspended for a certain length of time (i.e., a "drug holiday").

In some embodiments, administering is everlasting. As used herein, "everlasting" refers to the entire life of the subject ever since the subject has been determined to be predisposed to developing an IgE-related disease.

In some embodiments, administering starts or commences when the subject is one week old at most, two weeks old at most, three weeks old at most, four weeks old at most, 1 month old at most, 2 months old at most, or 3 months old at most, or any range therebetween. Each possibility represents a separate embodiment of the invention.

As used herein, the terms "subject" or "individual" or "animal" or "patient" or "mammal," refers to any subject, particularly a mammalian subject, for whom therapy is desired, for example, a human.

Pharmaceutical Composition for Modifying the Skin Microbiome

In one embodiment, a pharmaceutical composition for modifying the skin microbiome comprises a moisturizer. In another embodiment, the pharmaceutical composition for modifying the skin microbiome comprises an occlusive agent, an emollient, a humectant, or a combination thereof.

In one embodiment, the occlusive agent comprises carnauba wax, lanolin, mineral oil, olive oil, petrolatum, silicone, or a combination thereof. In one embodiment, the humectant comprises an alpha hydroxy acid, a hyaluronic acid, a sorbitol, urea, or a combination thereof. In another embodiment, the humectant comprises glycerin, a sugar, a protein, an amino acid, an elastin, a collagen, or a combination thereof.

In one embodiment, the emollient comprises collagen, colloidal oatmeal, elastin, glyceryl stearate, isopropyl palmitate, shea butter, stearic acid, or a combination thereof. In another embodiment, the emollient comprises a silicone, a vegetable oil, a butter, an alcohol, a petrolatum derivative, or a combination thereof. In one embodiment, the silicone comprises dimethicone, cyclomethicone, or a combination thereof. In one embodiment, the vegetable oil comprises grape seed oil, sesame seed oil, jojoba oil, olive oil, or a combination thereof. In one embodiment, the butter comprises cocoa butter, shea butter, or a combination thereof. In one embodiment, the alcohol comprises stearyl alcohol, acetyl alcohol, or a combination thereof. In one embodiment the petrolatum derivative comprises petroleum jelly, mineral oil, or a combination thereof.

In another embodiment, the present invention provides a method of suppressing, inhibiting, or proactively treating an IgE-related condition or disorder in a subject comprising the steps of: a) analyzing the microbiome on the skin of the subject; and b) administering a treatment for modifying the skin microbiome if a microbiome indicative of increased likelihood to develop IgE-related disease is detected.

In one embodiment, the treatment for modifying the skin microbiome comprises administering an emollient. In another embodiment, the treatment for modifying the skin microbiome as described herein comprises administering a food product to the subject. In one embodiment, the pharmaceutical composition for modifying the skin microbiome comprises a dietary supplement. In one embodiment, the food product is a snack bar, cookie, muffin, cake, bread, cereal, juice, yogurt, milk, dairy product, infant formula, and the like. In one embodiment, the food product for modifying the skin microbiome or the dietary supplement comprises one or more probiotics, one or more prebiotics, or a combination thereof.

In another embodiment, the present invention provides a method of altering the skin microbiome in a subject having or prone to developing an IgE-related disease, such as atopic dermatitis, comprising the step of administering a pharmaceutical composition for modifying the skin microbiome.

In another embodiment, the present invention provides a method of determining the effect of a pharmaceutical composition on the skin microbiome of a subject, comprising the steps of a) analyzing the microbiome in a first biological sample of the subject; b) administering the pharmaceutical composition to the subject, and c) analyzing the microbiome in a second biological sample of the subject, wherein a significant difference in the microbiome in the first biological sample of the subject compared to the microbiome in the second biological sample of the subject is indicative of the pharmaceutical composition is effective in altering the skin microbiome of the subject. In one embodiment, the composition comprises a moisturizer. In one embodiment, an increase in the bacterial heterogeneity in the sample is an indication that the pharmaceutical composition has a therapeutic or beneficial effect on the microbiome in the subject. In another embodiment, a decrease in the bacterial heterogeneity in the sample is an indication that the pharmaceutical composition has a deleterious effect on the microbiome in the subject.

In one embodiment, microbiome analysis as described herein comprises the detecting the presence or absence of microbes. In another embodiment, microbiome analysis comprises detecting the levels of microbes. In another embodiment, microbiome analysis comprises detection of the presence of absence of microbial genes. In another embodiment, microbiome analysis comprises detection of the levels of expression of microbial genes. In another embodiment, microbiome analysis comprises detection of a product generated by microbes of the microbiome. In one embodiment, the product comprises mRNA, a peptide or polypeptide or a protein, a carbohydrate, or a metabolite. In another embodiment, the product comprises short chain fatty acids (SCFAs).

As used herein, the term "metabolite" encompasses an intermediate or product of metabolism. The term "metabolite" is generally restricted to small molecules and does not include polymeric compounds such as DNA or proteins. A metabolite may serve as a substrate for an enzyme of a metabolic pathway, an intermediate of such a pathway, the product obtained by the metabolic pathway, or any combination thereof.

In one embodiment, a metabolite is selected from: sugars, organic acids, amino acids, fatty acids, hormones, vitamins, oligopeptides (less than about 100 amino acids in length), as well as ionic fragments thereof. In some embodiments, a metabolite is less than 3,000 Daltons in molecular weight. In some embodiments, a metabolite is 50 to 3,000 Daltons in molecular weight.

Computer Program Product

According to some embodiments, there is provided a computer program product for determining the predisposition of a subject to developing an IgE related disease, the computer program product comprising a non-transitory computer-readable storage medium having program instructions embodied therewith, the program instructions executable by at least one hardware processor to: receive a plurality of contribution factors comprising at least one contribution factor selected from parameter group 1 of Table 2 and at least one contribution factor selected from parameter groups 2 to 4 of Table 2; calculate a predisposition score based on the plurality of contribution factors; and determine the predisposition of the subject to developing an IgE related disease according to a predetermined threshold.

According to some embodiments, there is provided a computer program product for determining the predisposition of a subject to developing a food allergy, the computer program product comprising a non-transitory computer-readable storage medium having program instructions embodied therewith, the program instructions executable by at least one hardware processor to: receive a plurality of contribution factors comprising at least one contribution factor selected from parameter group 1 of Table 5 and at least one contribution factor selected from parameter groups 2 and 3 of Table 5; calculate a predisposition score based on the plurality of contribution factors; and determine the predisposition of the subject to developing an IgE related disease according to a predetermined threshold.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

In some embodiments, computer program of the present invention comprises Labview or MATLAB.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

Embodiments may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing embodiments in computer programming, and the embodiments should not be construed as limited to any one set of computer program instructions. Further, a skilled programmer would be able to write such a computer program to implement one or more of the disclosed embodiments described herein. Therefore, disclosure of a particular set of program code instructions is not considered necessary for an adequate understanding of how to make and use embodiments. Further, those skilled in the art will appreciate that one or more aspects of embodiments described herein may be performed by hardware, software, or a combination thereof, as may be embodied in one or more computing systems. Moreover, any reference to an act being performed by a computer should not be construed as being performed by a single computer as more than one computer may perform the act.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a", "an", and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Unless specifically stated or obvious from context, as used herein, the term "or" is understood to be inclusive.

Throughout this specification and claims, the word "comprise," or variations such as "comprises" or "comprising," indicate the inclusion of any recited integer or group of integers but not the exclusion of any other integer or group of integers.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

As used herein, the terms "comprises", "comprising", "containing", "having" and the like can mean "includes", "including", and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments. In one embodiment, the terms "comprises," "comprising," "having" are/is interchangeable with "consisting".

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Example 1

Efficacy of Daily Application of Skin Moisturizer Containing Acemannan Hydrogel in Preventing AD The inventors wanted to determine whether daily application of skin moisturizer containing Acemannan hydrogel on the skin of neonates who are at high-risk for development of AD is effective in reducing the cumulative incidence of AD at one year of age. Also, the inventors wanted to determine whether the treatment is effective in: reducing the cumulative incidence of AD at six months of age and/or at two years of age, delaying the onset of AD, reducing AD severity at one year of age, preventing food allergy occurrence at two years of age, preventing allergic rhinitis occurrence at three years of age, preventing asthma occurrence at three years of age and/or at six years of age, and assessing the development of the skin microbiome on infants receiving daily moisturizers versus those that do not and its correlation with disease occurrence and severity.

Therefore, the inventors perform a single-center, prospective, randomized, open-label, controlled study, as disclosed hereinbelow.

Baseline trans-epidermal water loss (TEWL) is be measured from the volar forearm and forehead in triplicate from each site using a Delfin Vapometer. Patients with mean volar forearm TEWL values below 8.5 g/m$^2$ are not randomized into this trial (screening failure). Patients with average volar forearm TEWL values of 8.50 g/m$^2$ or above are randomly assigned to either the control or interventional arm. Patients assigned to the control arm are given best practice skin care. Patients assigned to the interventional arm are given best practice skin care and are instructed to apply moisturizing lotion containing Acemannan on the infant's entire body daily for six months. Adverse event are collected through the intervention period and assessed by phone at visits V2-V5. Intervention compliance are be assessed via questionnaires at visits V2-V5.

All parents of participants are asked to fill out a lifestyle and environmental questionnaire at study enrollment. An additional lifestyle questionnaire is administered to parents of participants via telephone 4, 8, 12, 26 & 52 weeks from study enrollment.

Skin microbiome samples are collected from a subset (Control Arm n=25, Intervention Arm n=25) of trial participants at several timepoints: 4, 12, 26 & 52 weeks. The first 25 patients enrolled in each arm are selected for microbiome sampling. At 52 weeks, an additional 50 participants (Control Arm n=25, Intervention Arm n=25) are sampled. The first 50 patients from each arm of the trial are sampled at this timepoint. At all sampling sessions, separate samples are taken from the extensor aspects of the right hand, right forearm, cheek and nares.

Cumulative incidence of AD are evaluated using the UK refinement of the Hanifin and Rajka diagnostic criteria for atopic eczema. Evaluations are placed at 26 weeks, 52 weeks and 104 weeks from birth.

Age of atopic dermatitis onset is evaluated using the text of the validated question for disease onset of the UK refinement of the Hanifin and Rajka diagnostic criteria for atopic eczema, with changes to the answers to account for the age of the study population.

Food allergy (FA) assessment will be evaluated based on self-assessment. Study participants' parents are asked a set of question to assess FA development. FA assessment is placed at 52 and 104 weeks from study enrollment.

Assessment of cumulative incidence of allergic rhinitis and asthma takes place using the criteria set forth by the International Study of Asthma and Allergies in Childhood (ISAAC). The study proceeds until the last follow-up has been conducted.

Example 2

Topical Administration of Acemannan Reduce TEWL but not Beneficiary Bacterial Growth The inventors examined the activity of a composition comprising acemannan. The inventors performed an anti/pro microbial study, by culturing *Staphylococcus epidermidis* on a plate comprising acemannan. *S. epidermidis* is a skin resident who is known to play an important role in immune training and pathogen resistance. The results showed that acemannan did not affect the growth of *S. epidermidis* (FIG. 1). This supports the inventors' notion that the herein disclosed cream supports healthy colonization of the skin microbiome.

Further, the inventors showed that the disclosed cream reduced TEWL by 22%, on average (Table 7).

TABLE 7

| Summary of Acemannan topical administration experiment | | | |
|---|---|---|---|
| Subject | Baseline | After Application of Cream | Δ % |
| #1 | 10.5 | 7.3 | 30.5 |
| #2 | 7.1 | 8.8 | −24.0 |
| #3 | 9.6 | 9 | 6.3 |
| #4 | 185 | 19 | 89.7 |
| #5 | 11.2 | 10.1 | 9.8 |
| Average | 44.68 | 10.84 | 22.5 |

Example 3

Early Allergen Introduction Induced Toleronegicity and Skin Barrier Restoration Therapy Synergism Mice—BALB/c mice are bred and maintained on a special diet free of peanut, OVA, soy and cow's milk (the diet is made and supplied by Harlan Ltd, Bicester, UK). The mice are kept under specific pathogen-free conditions and provided water ad libitum. Female mice aged 6-8 weeks are used in this study (Group size=8 mice per group).

Peanut Protein—Partly de-fatted peanut flour is used to prepare concentrated peanut protein using a modification of the method described (de Jong et al.). Briefly, the flour is de-fatted with hexane five times and then extracted with 0.1 M $NH_4HCO_3$. The supernatant is removed and precipitated with 60% $(NH_4)_2SO_4$ for 2 h at 4° C. The precipitate is centrifuged, dissolved in a minimum volume of phosphate-buffered saline (PBS) and dialyzed extensively against PBS. This method uniformly yields 85-90% pure peanut protein. Peanut protein is biotinylated using standard methods.

Induction of peanut tolerance (Groups 2, 4, T=6 weeks old)—Animals are fed by gavage using a 20-gauge, 30 mm cannula. Each mouse receives a single intragastric feed of antigen dissolved in sterile PBS at a dose of 100 mg per mouse (5 mg per gram bodyweight).

Skin barrier disruption (Groups 1, 2, 3, 4, T=7 weeks old)—The stratum corneum was removed from both sides of the earlobe by application and removal of cellophane tape (Scotch™ (3M, Cergy-Pontoise Cedex, France)) five to eight times.

Skin barrier restoration therapy (Groups 3, 4, T=7 weeks old)—Immediately following skin barrier disruption, 12 hrs following skin barrier disruption, and immediately prior to epicutaneous sensitization (repeated throughout 72 hr period of epicutaneous sensitization described below), Cura+ lotion (Provided by MyOR) is applied to the disturbed earlobe.

Epicutaneous sensitization (Groups 1, 2, 3, 4, T=24 hrs after skin barrier disruption)—Twenty-four hours after skin barrier disruption, 25 mL of peanut protein in PBS (4 mg/mL) are applied to both sides of the earlobe with a cotton bud. The application of peanut protein to the skin is repeated on the next 2 consecutive days. An estimated maximum of 100 mg of protein is deposited on the ear by this technique. Antigen applied to intact skin that has not been tape stripped and PBS without antigen applied to stripped skin and intact skin are included as controls.

Delayed-type hypersensitivity (DTH) response (Groups 1, 2, 3, 4, T=10 weeks old)—Mice are challenged 20 days after the epicutaneous sensitization by an injection of 100 mg peanut protein in PBS into the left hind footpad. Net footpad swelling is measured using a microcalliper (Mitutoyo, Siwa, Japan) 24 h after challenge. Mice are euthanized after the 24 h footpad measurement. Spleen and lymph node cell suspensions are obtained by mechanical disaggregation, and $2\times10^5$ cells cultured in 96-well flat-bottom plates in a total volume of 200 mL RPMI1640 medium supplemented with 10% FCS, 50 mM 2-ME and 5 mg/mL gentamycin. Peanut protein is added at concentrations ranging from 5 to 450 mg/mL. Control responses to a control antigen (OVA) or Concanavalin A (ConA) at 1 mg/mL are also determined. Cultures are incubated at 37° C. for 90 h and pulsed with 1 mCi of [$^3$H]-thymidine (Amersham Pharmacia, Little Chalfont, UK) for the last 18 h. Cells are harvested, and thymidine incorporation is determined by liquid scintillation counting on a MicroBeta (Wallac, Turku, Finland). Supernatants are assayed by enzyme-linked immunosorbent assay (ELISA) for interleukin (IL)-4, IL-10, interferon gamma (IFN-γ) and transforming growth factor-betta (TGF-β) using antibodies from PharMingen (San Diego, CA, USA), according to the manufacturer's protocol. Recombinant mouse IL-4, IL-10 and IFN-γ and recombinant human TGF-β1 from PharMingen were used as standards. The detection limit of the assays was 5 pg/mL for IL-4 and 40 pg/mL for IL-10, IFN-γ and TGF-β.

Antibody responses (Groups 1, 2, 3, 4, T=10 weeks old)—At the end of each experiment, mice are bled by cardiac puncture and sera prepared for specific antibody determinations. For IgG and IgG1/2a antibodies, 96-well Maxosorbplates (Nunc, Roskilde, Denmark) are coated with peanut protein at 250 mg/mL in carbonate bicarbonate buffer (CBB) at 4° C. overnight. Appropriately diluted sera are added (100 mL in PBS) and the plates incubated at 37° C. for 90 min. After washing, alkaline phosphatase-conjugated polyclonal goat anti-mouse IgG Fc (Sigma, Gillingham, UK), rat monoclonal antibody to mouse IgG1 (Zymed, San Francisco, CA, USA) or rat monoclonal antibody to IgG2a (PharMin-gen) is added for 1 h at 37° C. The alkaline phosphatase substrate pNPP (Sigma) is then added and absorbance is measured at 405 nm. Antigen-specific IgE is measured by an IgE capture method. Sera to be tested are added to Maxisorb microtitre plate wells coated with 1 mg/mL of rat monoclonal anti-mouse IgE (PharMingen). Biotinylated peanut is then added at a concentration of 10 mg/mL and incubated for 2 h at 37° C. After washing, alkaline phosphatase streptavidin (PharMingen) is added for 1 h followed by pNPP substrate.

Figures 3A, 3B, 3C, 3D:
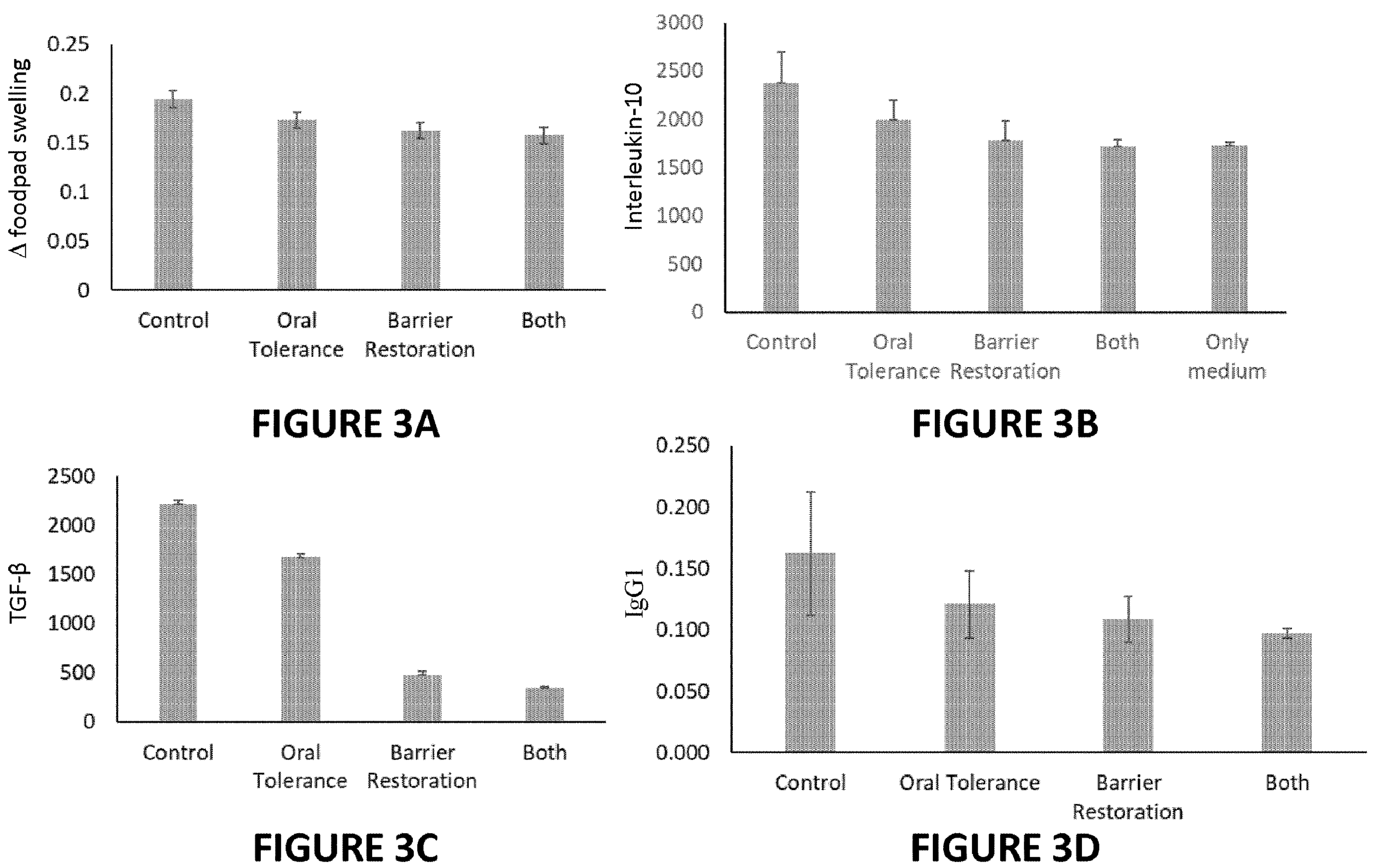
FIGS. 3A-3D include vertical bar graphs showing the effects of oral tolerance, epicutaneous sensitization, or both, on footpad swelling (3A), interleukin 10 (IL-10) secretion (3B), transformation growth factor beta (TGF-β; 3C), and IgG1 levels (3D).

Epicutaneous allergen introduction generates a predominant Th2 response characterized by high levels of IgG1 and no detectable IgG2a, footpad swelling DTH response, and IL-10 and TGF-B induction. This response was mitigated partially by either skin barrier restoration therapy following skin barrier disruption, yet prior to epicutaneous sensitization or by early oral introduction of peanuts prior to skin barrier disruption and restoration therapy (FIG. 3). A further reduction in the Th2 response was observed using both skin barrier restoration therapy and early oral introduction of allergens (FIG. 3). Taken together, these results show the potential of skin barrier restoration therapy alone, or in combination with early introduction of allergens to mitigate the Th2 response characteristic of IgE mediated allergic conditions.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

What is claimed is:

1. A method for reducing the susceptibility, delaying, suppressing, or treating an IgE-related disease selected from the group consisting of: atopic dermatitis, allergic asthma, allergic rhinitis, food allergy, eczema, lupus, rheumatoid arthritis, psoriasis, psoriasis vulgaris, acne, acne vulgaris, rosacea, skin and soft tissue infections, dandruff, blepharitis, tinea versicolor, and any combination thereof, in a subject, the method comprising:

a. selecting a subject at risk of developing an IgE-related disease; and b. topically administering to said subject a therapeutically effective amount of a composition comprising acemannan in an amount ranging from 0.1 to 1.0% w/w and orally administering to said subject a therapeutically effective amount of a composition comprising peanut protein, and wherein said topically administering, orally administering, or both, starts when said subject is one year old, at most, thereby reducing susceptibility, delaying, suppressing, or treating an IgE-related disease in the subject.

2. The method of claim 1, wherein said selecting comprises a step of determining: (c) whether said subject is or was exposed to pollution.

3. The method of claim 1, wherein said composition comprising acemannan is a cream.

4. The method of claim 1, wherein said topically administering comprises reducing transepidermal water loss (TEWL) by at least 20% in said subject.

5. The method of claim 1, wherein said topically administering, orally administering, or both, is daily administering.

6. The method of claim 1, wherein said topically administering, orally administering, or both, is for a period of 2 weeks to 72 months.

7. The method of claim 1, wherein said subject is one month old at most.

* * * * *